United States Patent
Cook et al.

(10) Patent No.: US 7,666,845 B2
(45) Date of Patent: Feb. 23, 2010

(54) COMPOUNDS HAVING INHIBITORY ACTIVITY AGAINST SODIUM-DEPENDENT GLUCOSE TRANSPORTER

(75) Inventors: Kevin L. Cook, San Diego, CA (US); Heng-Keang Lim, Lawrenceville, NJ (US); Frank J. Villani, Perkasie, PA (US); Lorraine Scott, North Wales, PA (US); Christian Andrew Baumann, Exton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 154 days.

(21) Appl. No.: 11/949,236

(22) Filed: Dec. 3, 2007

(65) Prior Publication Data
US 2009/0029927 A1 Jan. 29, 2009

Related U.S. Application Data

(60) Provisional application No. 60/868,368, filed on Dec. 4, 2006.

(51) Int. Cl.
*A61K 31/7012* (2006.01)
*C07H 15/26* (2006.01)
*A61P 3/10* (2006.01)

(52) U.S. Cl. .......................... 514/23; 536/54; 536/122
(58) Field of Classification Search ........................ None
See application file for complete search history.

(56) References Cited

U.S. PATENT DOCUMENTS

| | | | |
|---|---|---|---|
| 5,424,406 | A | 6/1995 | Tsujihara et al. |
| 5,731,292 | A | 3/1998 | Tsujihara et al. |
| 5,830,873 | A | 11/1998 | Tsujihara et al. |
| 6,414,126 | B1 | 7/2002 | Ellsworth et al. |
| 6,515,117 | B2 | 2/2003 | Ellsworth et al. |
| 6,562,791 | B1 | 5/2003 | Maurya et al. |
| 2001/0041674 | A1 | 11/2001 | Tomiyama et al. |
| 2002/0052326 | A1 | 5/2002 | Washburn |
| 2002/0111315 | A1 | 8/2002 | Washburn et al. |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2004/0053855 | A1 | 3/2004 | Fujikura et al. |
| 2004/0063646 | A1 | 4/2004 | Fujikura et al. |
| 2004/0110936 | A1 | 6/2004 | Ohsumi et al. |
| 2004/0116357 | A1 | 6/2004 | Fushimi et al. |
| 2004/0132669 | A1 | 7/2004 | Nishimura et al. |
| 2004/0138143 | A1 | 7/2004 | Glombik et al. |
| 2004/0259819 | A1 | 12/2004 | Frick et al. |
| 2005/0014704 | A1 | 1/2005 | Frick et al. |
| 2005/0032711 | A1 | 2/2005 | Patel et al. |
| 2005/0032712 | A1 | 2/2005 | Urbanski |
| 2005/0037980 | A1 | 2/2005 | Rybczynski et al. |
| 2005/0037981 | A1 | 2/2005 | Beavers et al. |
| 2005/0233988 | A1* | 10/2005 | Nomura et al. ............... 514/43 |
| 2006/0035841 | A1* | 2/2006 | Eckhardt et al. ............... 514/23 |
| 2006/0122126 | A1 | 6/2006 | Imamura et al. |
| 2006/0217323 | A1 | 9/2006 | Patel et al. |
| 2006/0229260 | A1 | 10/2006 | Rybczynski et al. |
| 2006/0234954 | A1 | 10/2006 | Urbanski |
| 2006/0293251 | A1 | 12/2006 | Urbanski et al. |
| 2007/0060545 | A1 | 3/2007 | Nomura et al. |
| 2008/0027122 | A1 | 1/2008 | Nomura et al. |

FOREIGN PATENT DOCUMENTS

| | | |
|---|---|---|
| CA | 2 494 177 A1 | 2/2004 |
| EP | 1 528 066 A1 | 5/2005 |
| JP | 2001-288178 A | 10/2001 |
| JP | 2003-12686 A1 | 1/2003 |
| WO | WO 01/27128 | 4/2001 |
| WO | WO 01/68660 A1 | 9/2001 |
| WO | WO 01/74834 A1 | 10/2001 |
| WO | WO 01/74835 A1 | 10/2001 |
| WO | WO 02/053573 A1 | 7/2002 |
| WO | WO 02/068439 A1 | 9/2002 |
| WO | WO 02/068440 A1 | 9/2002 |
| WO | WO 02/083066 A2 | 10/2002 |
| WO | WO 02/088157 A1 | 11/2002 |
| WO | WO 03/011880 A1 | 2/2003 |
| WO | WO 03/020737 A1 | 3/2003 |
| WO | WO 03/099836 A1 | 12/2003 |
| WO | WO 2004/007517 A1 | 1/2004 |
| WO | WO 2004/013118 A1 | 2/2004 |
| WO | WO 2004/014931 A1 | 2/2004 |
| WO | WO 2004/019958 A1 | 3/2004 |
| WO | WO 2004/052903 A1 | 6/2004 |

(Continued)

OTHER PUBLICATIONS

Unger et al. "Hyperglycemia as an inducer as well as a consequence of impaired islet cell function and insulin resistance: implications for the management of diabetes" Diabetologia, vol. 28, p. 119-121 (1985).

(Continued)

*Primary Examiner*—Shaojia Anna Jiang
*Assistant Examiner*—Bahar Schmidtmann

(57) ABSTRACT

The invention is directed to compounds of the formula (I) described herein, a pharmaceutically acceptable salt thereof, or a prodrug thereof, and pharmaceutical compositions and methods of treatment.

(I)

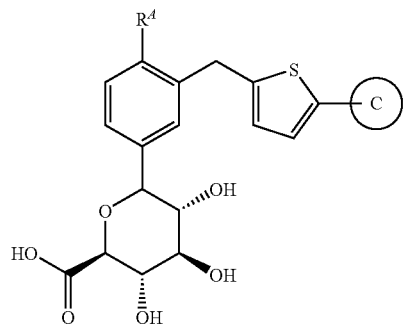

16 Claims, No Drawings

FOREIGN PATENT DOCUMENTS

| | | |
|---|---|---|
| WO | WO 2004/080990 A1 | 9/2004 |
| WO | WO 2005/012326 | 2/2005 |
| WO | WO 2006/010557 | 2/2006 |
| WO | WO 2008/013322 A1 | 1/2008 |

OTHER PUBLICATIONS

Rossetti et al. "Glucose Toxicity"; Diabetes Care, vol. 13, p. 610-630 (1990).

Rossetti et al. Correction of Hyperglycemia with Phlorizin Normalizes Tissue Sensitivity to Insulin in diabetic rats Journal of Clinical Investigation, vol. 79, p. 1510-1515 (1987).

Rossetti et al. Effect of Chronic Hyperglycemia on In Vivo Insulin Secretion in Partially Pancreatectomized Rats Journal of Clinical Investigation, vol. 80, p. 1037-1044 (1987).

Kahn et al. "Normalization of Blood Glucose in Diabetic Rats with Phlorizin Treatment Reverses Insulin-resistant Glucose Transport in Adipose Cells without Restoring Glucose Transporter Gene Expression" Journal of Clinical Investigation, vol. 87, p. 561-570 (1991).

Tsujihara et al. "Na+ Glucose Cotransporter (SGLT) Inhibitors as Antidiabetic Agents. 4. Synthesis and Pharmacological Properties of 4'-Dehydroxyphlorizin Derivatives Substituted on the B Ring" Journal of Medicinal Chemistry, vol. 42, p. 5311-5324 (1999).

Arakawa et al, Improved diabetic syndrome in C57BL/KsJ-db/db Mice By Oral Administration of the Na+– Glucose Cotransporter Inhibitor T-1095: British Journal of Pharmacology, vol. 132, p. 578-586 (2001).

Ueta et al. "Long-term treatment with the Na+–glucose contransporter inhibitor T1095 causes sustained improvement in hyperglycemia and prevents diabetic neuropathy in Goto-Kakizaki Rats" Life Sci., 76(23): 2655-68 (2005), etc.

Roshan Ahmad et al., Nucleosides, Nucleotides & Nucleic Acids, vol. 20, No. 9, (2001), pp. 1671-1682.

Khosrow Zamani et al., Journal of the Chinese Chemical Society, vol. 49, (2002), pp. 1041-1044.

Galal T. Maatooq et al., Phytochemistry, vol. 44, No. 1, (Jan. 1997), pp. 187-190.

Hongu et al., Chem. Pharm. Bull., vol. 46, No. 1, pp. 22-33, (1998).

PCT International Search Report dated Apr. 16, 2008 for PCT/US2007/086247 which relates to U.S. Appl. No. 11/949,236.

* cited by examiner

COMPOUNDS HAVING INHIBITORY ACTIVITY AGAINST SODIUM-DEPENDENT GLUCOSE TRANSPORTER

CROSS-REFERENCE TO RELATED APPLICATIONS

This application claims priority from U.S. Provisional Application No. 60/868,368, filed Dec. 4, 2006, the disclosure of which is hereby incorporated by reference in its entirety.

STATEMENT REGARDING FEDERALLY SPONSORED RESEARCH OR DEVELOPMENT

The research and development of the invention described below was not federally sponsored.

TECHNICAL FIELD

The present invention relates to novel compounds having an inhibitory activity against sodium-dependent glucose transporter (SGLT) being present in the intestine or kidney.

BACKGROUND OF THE INVENTION

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated [cf., Diabetologia, vol. 28, p. 119 (1985); Diabetes Care, vol. 13, p. 610 (1990), etc.]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), Ueta, Ishihara, Matsumoto, Oku, Nawano, Fujita, Saito, Arakawa, Life Sci., 76(23): 2655-68 (2005), etc.].

From the above, SGLT inhibitors may be expected to improve insulin secretion and insulin resistance by decreasing the blood glucose level in diabetic patients and further prevent the onset and progress of diabetes mellitus and diabetic complications.

WO 01/27128 discloses an aryl C-glycoside compound having the following structure:

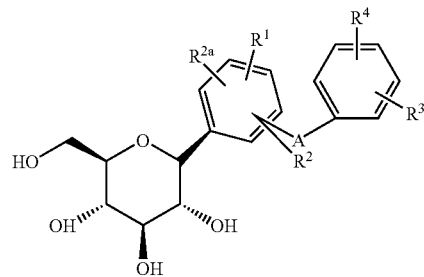

This compound is disclosed to be useful in the prophylaxis or treatment of diabetes mellitus, etc., as an SGLT inhibitor.

SUMMARY OF THE INVENTION

In one aspect, the present invention is directed to a compound of formula (I):

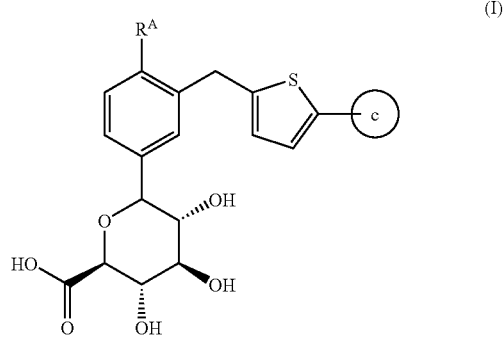

wherein $R^A$ is a halogen atom, or a lower alkyl group; and

Ring c is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group;

or a pharmaceutically acceptable salt thereof, or a prodrug thereof.

In another aspect, the present invention is directed to pharmaceutical compositions containing one or more compounds of Formula (I), pharmaceutically acceptable salts or prodrugs thereof.

In yet another aspect, the present invention is directed to a method for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the compound of Formula (I), a pharmaceutically acceptable salt thereof, or a prodrug thereof as set forth herein.

DETAILED DESCRIPTION OF THE INVENTION

The present invention relates to a compound of the following formula (I), or a pharmaceutically acceptable salt thereof, or a prodrug thereof:

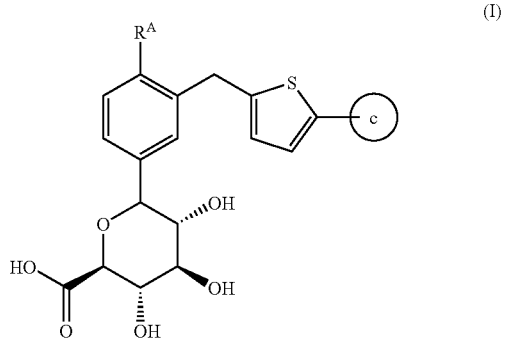

wherein
$R^A$ is a halogen atom, or a lower alkyl group; and
Ring c is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

The compound of the formula (I) exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing.

Hereinafter, the present compound (I) is illustrated in more detail.

The definitions for each term used in the description of the present invention are listed below.

The term "halogen atom" or "halo" means chlorine, bromine, fluorine and iodine, and chlorine and fluorine are preferable.

The terms "alkyl" and "alkyl group" mean a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc.

Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "heterocyclyl" or "heterocyclyl group" means a monovalent group of an unsaturated monocyclic heterocyclic ring or unsaturated fused heterobicyclic ring and a monovalent group of the saturated version of an unsaturated monocyclic heterocyclic or unsaturated fused heterobicyclic ring.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydro-isoquinoline, etc. Further, the "heterocyclic ring" also includes possible N- or S-oxides thereof.

The term "alkoxy group" means ones formed by binding an "alkyl group" to an oxygen atom.

The terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl) aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound (I) includes an intramolecular salt, hydrate, solvate or polymorphism thereof.

In a preferable embodiment, Ring c is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group. In particular, Ring c is a phenyl group substituted by a halogen atom, a cyano group, a lower alkyl group, a halo-lower alkyl group, a lower alkoxy group, or a halo-lower alkoxy group; or a heterocyclyl group substituted by a halogen atom, a cyano group, a lower alkyl group, or a lower alkoxy group. More particularly, Ring c is a phenyl group substituted by a halogen atom or a cyano group, or a pyridyl group substituted by a halogen atom.

In another preferable embodiment, the heterocyclyl group is a thienyl group, a pyridyl group, a pyrimidinyl group, a pyrazinyl group, pyrazolyl group, a thiazolyl group, a quinolyl group, a tetrazolyl group, or an oxazolyl group.

In another preferable embodiment, $R^A$ is $C_{1-3}$alkyl. More particularly, $R^A$ is methyl.

In another preferable embodiment, $R^A$ is halogen. More particularly, $R^A$ is chloro.

In another preferable embodiment, Ring c is a phenyl group substituted by a halogen atom. More particularly, the halogen atom is F.

In another preferable embodiment, Ring c is a pyridyl group substituted by a halogen atom. More particularly, the halogen atom is F.

In particular, $R^A$ is $C_{1-3}$alkyl and Ring c is a phenyl group substituted by a halogen atom. More particularly, $R^A$ is methyl and Ring c is a phenyl group substituted by F.

In another preferable embodiment, $R^A$ is halogen and Ring c is a pyridyl group substituted by a halogen atom. More particularly, $R^A$ is chloro and Ring c is a pyridyl group substituted by F.

In another preferable embodiment, the compound of the present invention is selected from the group consisting of 6-{3-[5-(4-fluoro-phenyl)-thiophen-2-yl methyl]-4-methyl-phenyl}-3,4,5-trihydroxy-tetrahydro-pyran-2-carboxylic acid and 6-{4-Chloro-3-[5-(6-fluoro-pyridin-3-yl)-thiophen-2-ylmethyl]-phenyl}-3,4,5-trihydroxy-tetrahydro-pyran-2-carboxylic acid; or a pharmaceutically acceptable salt thereof, or prodrug thereof.

Furthermore, the compound of the following structure

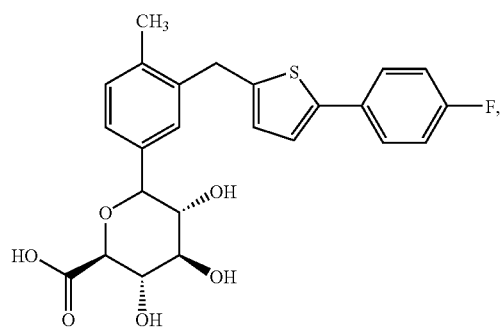

is a preferred embodiment of the present invention.

Furthermore, the compound of the following structure

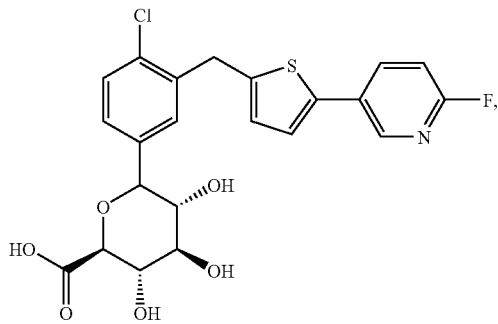

is a preferred embodiment of the present invention.

The compound (I) of the present invention exhibits an inhibitory activity against sodium-dependent glucose transporter, and blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compound (I) of the present invention, a pharmaceutically acceptable salt thereof, or prodrug thereof may be administered either orally or parenterally, and can be used in the form of a suitable pharmaceutical composition. Suitable pharmaceutical compositions for oral administration includes, for example, solid preparation such as tablets, granules, capsules, powders, etc., or solution preparations, suspension preparations, or emulsion preparations, etc. Suitable pharmaceutical compositions for parenteral administration includes, for example, suppositories; injection preparations and intravenous drip preparations using distilled water for injection, physiological saline solution or aqueous glucose solution; or inhalant preparations. Generally the compound will be administered in admixture with a pharmaceutical carrier, excipient or diluent selected with regard to the intended route of administration. By way of example, in the pharmaceutical compositions of the present invention, the compounds of the present invention may be admixed with any suitable binder(s), lubricant(s), suspending agent(s), coating agent(s), and/or solubilising agent(s). Tablets or capsules of the compounds may be administered singly or two or more at a time, as appropriate. It is also possible to administer the compounds in sustained release formulations.

The dosage of the present compound (I) or a pharmaceutically acceptable salt thereof may vary according to the administration routes, ages, body weight, conditions of a patient, or kinds and severity of a disease to be treated, and it is usually in the range of about 0.1 to 50 mg/kg/day, preferably in the range of about 0.1 to 30 mg/kg/day.

The compound of the formula I may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RXR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula (I) may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

The present invention also relates to a method for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the compound of formula (I), a pharmaceutically acceptable salt thereof, or a prodrug thereof.

The present invention also relates to a method for treatment of type 1 or 2 diabetes mellitus, which comprises administering to a mammalian species in need of treatment a therapeutically effective amount of the compound of formula (I), or a pharmaceutically acceptable salt thereof, or a prodrug thereof alone, or in combination with another antidiabetic agent, an agent for treating diabetic complications, an anti-obesity agent, an antihypertensive agent, an antiplatelet agent, an anti-atherosclerotic agent and/or a hypolipidemic agent.

The present compound of the formula (I) may be prepared from the following compounds:

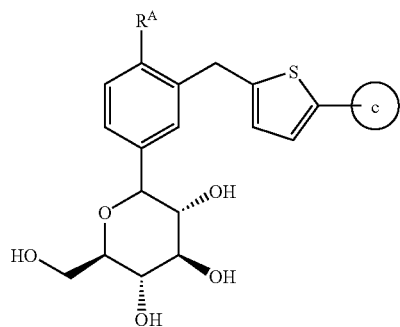

which in turn can be prepared according to US20050233988 to Nomura et al., which is hereby incorporated by reference in its entirety.
Specifically, compounds of the formula (I) can be prepared by the processes in scheme A below, wherein $R^A$ and Ring c are as described above:
scheme A
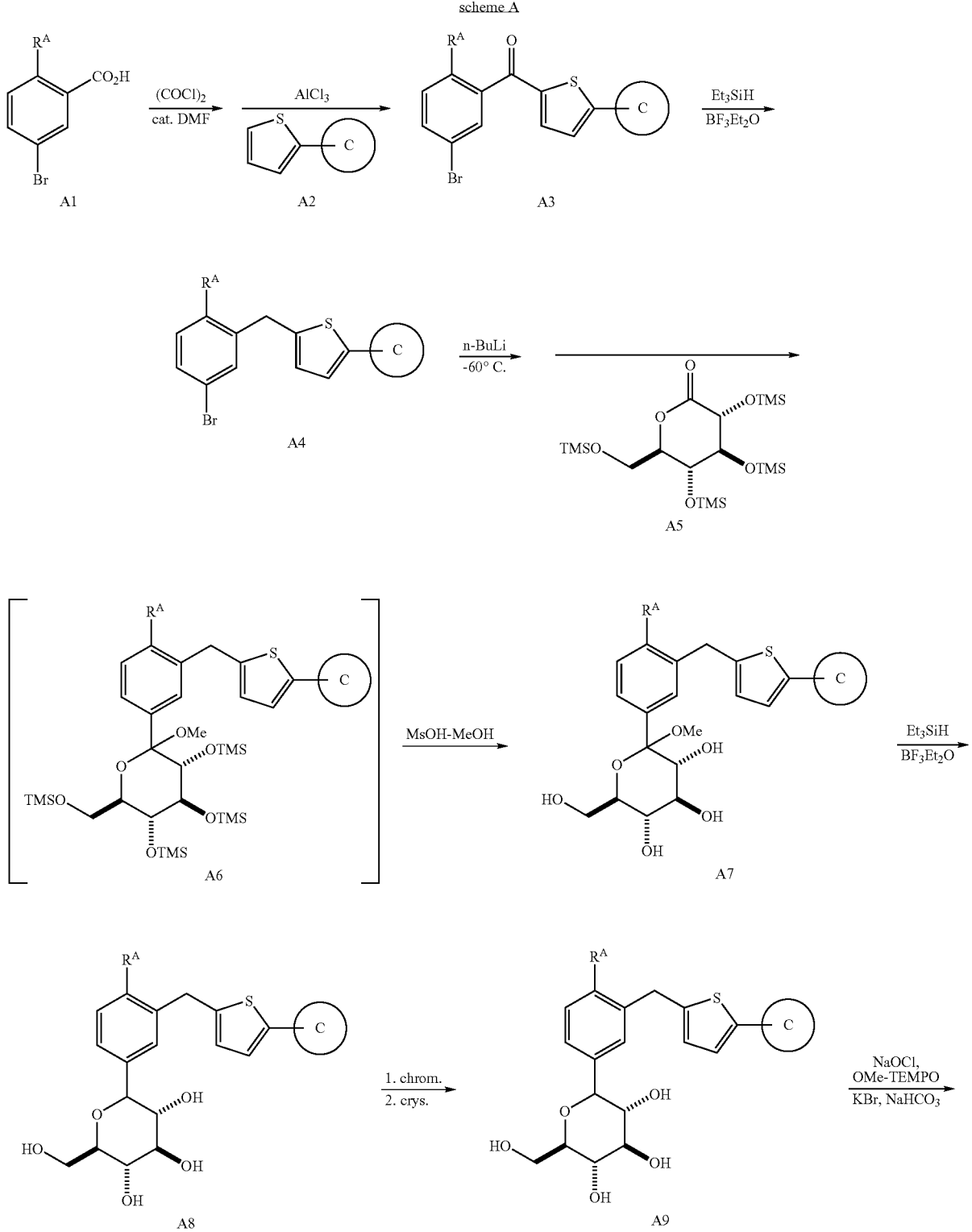

-continued

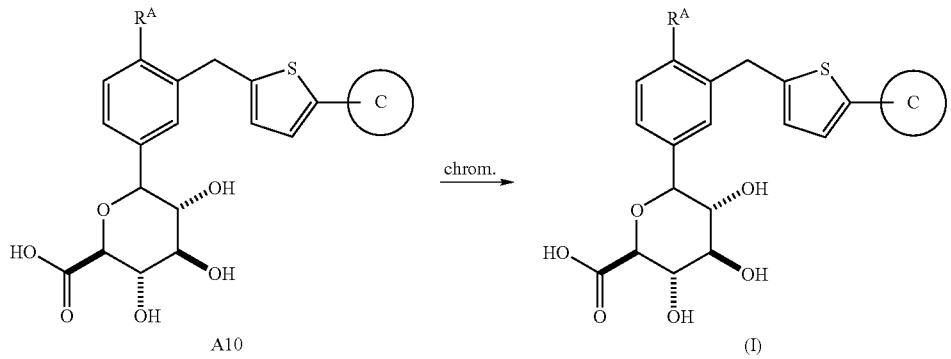

Compounds of Formula (I) can be prepared by treating commercially available compounds of formula A1 preferably with a catalyst such as N,N-dimethylformamide (DMF) and oxalyl chloride in dichloromethane at ambient temperature to obtain the corresponding acid chlorides which are reacted with compounds of formula A2 preferably under Friedel-Craft conditions to give compounds of formula A3. Compounds of formula A3 are treated with reducing agents such as triethylsilane in a solvent such as dichloromethane or acetonitrile or mixtures thereof preferably containing a catalyst such as boron trifluoride diethyl etherate at preferably 0-20° C. Compounds of formula A4 are activated for coupling by treatment with preferably n-BuLi at preferably −60° C. to −70° C. in a solvent such as THF, heptane, toluene, methylcyclohexane, or mixtures thereof prior to addition of lactone A5. Subsequent reaction with methane sulfonic acid in methanol affords compounds of formula A7. Compounds of formula A7 are treated with reducing agents such as triethylsilane in a solvent such as dichloromethane, acetonitrile, or toluene or mixtures thereof containing preferably a catalyst such as boron trifluoride diethyl etherate or trifluoroacetic acid at preferably −30° C. to rt. Compounds of formula A8 can be purified via column chromatography and crystallized from a solvent such as ethyl acetate, ethanol, methanol, or heptane or mixtures thereof. Compounds of formula A9 are treated with a catalytic amount of 4-methoxy-TEMPO free radical and sodium hypochlorite in the presence of potassium bromide and a saturated sodium bicarbonate solution to give a crude mixture of compounds of formula A10 which can be purified by column chromatography to yield the title compounds.

The starting compound and agents in the method described above are commercially available or are well known in the art, or may easily be prepared by a standard method well known to an ordinary skilled person in this field from one or more commercially available or known compounds.

Hereinafter, the present invention will be illustrated by the Examples, but the present invention should not be construed to be limited thereto.

EXAMPLE 1

6-{3-[5-(4-Fluoro-phenyl)-thiophen-2-ylmethyl]-4-methyl-phenyl}-3,4,5-trihydroxy-tetrahydro-pyran-2-carboxylic acid

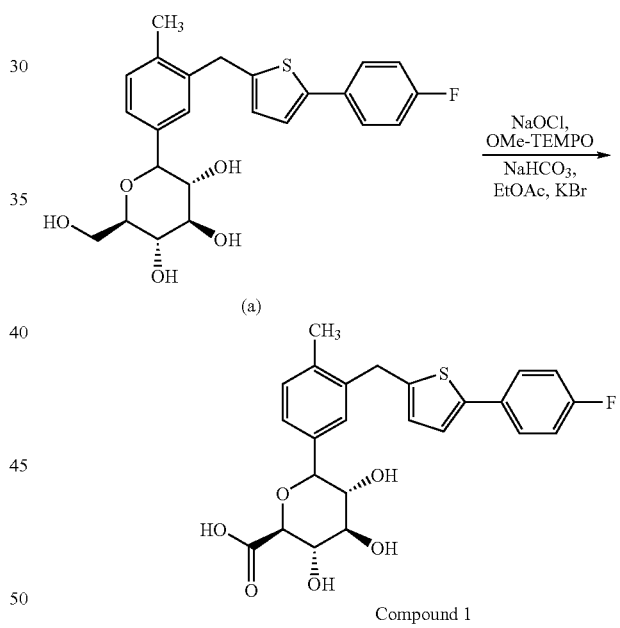

Compound (a) above was made according to the processes and examples disclosed in US20050233988 A1 to Nomura et al. is incorporated by reference hereby in its entirety.

To a cooled (0° C.) mixture of Compound (a) (20.0 g. 44.8 mmol) in ethyl acetate (160 mL) containing 4-methoxy-TEMPO (200.0 mg, 1.06 mmol) and potassium bromide (556 mg, 4.66 mmol) was added a solution of saturated aqueous sodium bicarbonate (100 mL) and sodium hypochlorite (28.0 mL, 37.6-48.8 mmol), dropwise, such that the temperature did not exceed 10° C. A sample was taken 30 minutes after the end of the addition, diluted with 1N HCl and extracted with EtOAc. HPLC analysis (35SGLT) showed a 1:1 mixture of Compound (a) and Compound 1. After an hour of stirring between 0-15° C., additional sodium hypochlorite (10-13%, 5.00 mL, 6.71-8.73 mmol) was added dropwise. Stirring was continued for another 1-1.5 hr. HPLC analysis still showed starting material present. Additional sodium hypochlorite (10-13%, 5.00 mL, 6.71-8.73 mmol) was slowly added. A sample was taken after 30 minutes. Additional sodium hypochlorite (10-13%, 5.00 mL, 6.71-8.73 mmol) was slowly added. The ice bath was removed and the opaque yellow colored mixture was stirred at ambient temperature for 1.0 hr. The mixture was diluted with 0.5N HCl (200 mL) and ethyl acetate (100 mL). An emulsion developed; the mixture was left to separate over night.

The layers were separated and the aqueous extracted with EtOAc (3×100 mL). The organic layer was dried and concentrated down to approximately 100 mL of solvent remained then 80 g of silica gel was added and the mixture was concentrated to dryness. Flash chromatography using 2% MeOH/EtOAc on a 220 g silica gel column resulted in 6.49 g (31.81% yield) of a yellow solid (Compound 1).

EXAMPLE 2

Biological Example

Assay

Method:

CHOK1 cells expressing human SGLT2 were seeded in 96-well white walled plates at a density of 50,000 cells/well in F-12 nutrient mixture (Ham's F-12) containing 10% fetal bovine serum, 400 µg/ml Geneticin, 50 units/ml sodium penicillin G (Gibco-BRL) and 50 µg/ml streptomycin sulfate. After 2 days of culture at 37° C. in a humidified atmosphere containing 5% $CO_2$, cells were washed once with the assay buffer (137 mM NaCl, 5 mM KCl, 1 mM $CaCl_2$, 1 mM $MgCl_2$, 50 mM Hepes, and 20 mM Tris, pH 7.4) and incubated with 80 µl of the buffer containing test compounds for 10 min at 37° C. Test compounds were dissolved in DMSO. The final concentration of DMSO was 0.5%. The transport reaction was initiated by addition of 20 µl [$^{14}$C]-methyl-α-D-glucopyranoside ($^{14}$C-AMG, 0.08 uCi per well) solution (final concentration, 0.5 mM). After incubation for 2 hours at 37° C., the uptake was stopped by aspiration of the incubation mixture, the cells were washed three times with ice-cold PBS. Then, cells were solubilized with 0.3 N NaOH and scintalin was added for determination of radioactivity by a liquid scintillation counter. Nonspecific AMG uptake was defined as that which occurred in the presence of 100 µM of phlorizin, a specific inhibitor of sodium-dependent glucose cotransporter. Specific uptake was normalized for the protein concentrations measured by the method of Bradford. The 50% inhibitory concentration ($IC_{50}$) values were calculated from dose-response curves by least square method.

Compound 1 was tested in the above assay with the following results:

Results: Human SGLT2 inhibition $IC_{50}$=1.1 µM

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of formula (I)

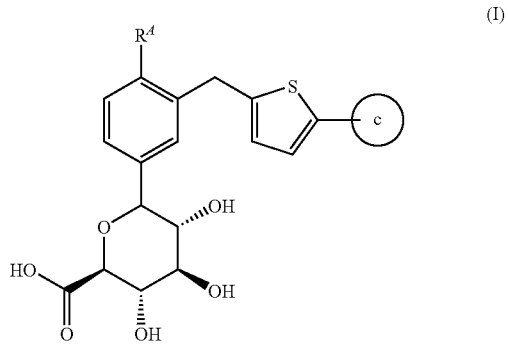

wherein $R^A$ is a halogen atom, or a lower alkyl group; and

Ring c is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group;

or a pharmaceutically acceptable salt thereof.

2. The compound or the pharmaceutically acceptable salt thereof, according to claim 1, wherein Ring c is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

3. The compound or the pharmaceutically acceptable salt thereof, according to claim 2, wherein Ring c is a phenyl group substituted by a halogen atom, a cyano group, a lower alkyl group, a halo-lower alkyl group, a lower alkoxy group, or a halo-lower alkoxy group; or a heterocyclyl group substituted by a halogen atom, a cyano group, a lower alkyl group, or a lower alkoxy group.

4. The compound or the pharmaceutically acceptable salt thereof, according to claim 1, wherein the heterocyclyl group is a thienyl group, a pyridyl group, a pyrimidinyl group, a pyrazinyl group, pyrazolyl group, a thiazolyl group, a quinolyl group, a tetrazolyl group, or an oxazolyl group.

5. The compound or the pharmaceutically acceptable salt thereof, according to claim 1, wherein Ring c is a phenyl group substituted by a halogen atom or a cyano group, or a pyridyl group substituted by a halogen atom.

6. The compound or the pharmaceutically acceptable salt thereof, according to claim 1, wherein $R^A$ is $C_{1-3}$alkyl.

7. The compound or the pharmaceutically acceptable salt thereof, according to claim 1, wherein Ring c is a phenyl group substituted by a halogen atom.

8. The compound or the pharmaceutically acceptable salt thereof, according to claim 1, wherein $R^A$ is $C_{1-3}$alkyl and Ring c is a phenyl group substituted by a halogen atom.

9. The compound or the pharmaceutically acceptable salt thereof, according to claim 8, wherein $R^A$ is methyl and Ring c is a phenyl group substituted by F.

10. The compound or the pharmaceutically acceptable salt thereof according to claim 1 wherein the compound is 6-{3-[5-(4-fluoro-phenyl)-thiophen-2-ylmethyl]-4-methyl-phenyl}-3,4,5-trihydroxy-tetrahydro-pyran-2-carboxylic acid; or the pharmaceutically acceptable salt thereof.

11. The compound or the pharmaceutically acceptable salt thereof according to claim 1 wherein $R^A$ is halogen.

12. The compound or the pharmaceutically acceptable salt thereof according to claim 1 wherein Ring c is a pyridyl group substituted by a halogen atom.

13. The compound or the pharmaceutically acceptable salt thereof according to claim 1 wherein $R^A$ is chloro and Ring c is a pyridyl group substituted by F.

14. The compound or the pharmaceutically acceptable salt thereof, according to claim 1 wherein the compound is 6-{4-Chloro-3-[5-(6-fluoro-pyridin-3-yl)-thiophen-2-ylmethyl]-phenyl}-3,4,5-trihydroxy-tetrahydro-pyran-2-carboxylic acid; or the pharmaceutically acceptable salt thereof.

15. A pharmaceutical composition, which comprises the compound as set forth in claim 1, or the pharmaceutically acceptable salt thereof in admixture with a pharmaceutical carrier, excipient or diluent.

16. A method for treating or delaying the progression or onset of diabetes mellitus, diabetic retinopathy, diabetic neuropathy, diabetic nephropathy, delayed wound healing in a patient having diabetes, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the compound, or the pharmaceutically acceptable salt thereof as set forth in claim 1.

* * * * *